(12) United States Patent
Fishman et al.

(10) Patent No.: US 9,724,364 B2
(45) Date of Patent: Aug. 8, 2017

(54) AEROSOL HYDOGEN PEROXIDE MIXTURE WITH TRIGGER SPRAYER

(71) Applicants: Michael Fishman, Coral Springs, FL (US); Neal Markus, Hollywood, FL (US)

(72) Inventors: Michael Fishman, Coral Springs, FL (US); Neal Markus, Hollywood, FL (US)

( * ) Notice: Subject to any disclaimer, the term of this patent is extended or adjusted under 35 U.S.C. 154(b) by 397 days.

(21) Appl. No.: 14/575,588

(22) Filed: Dec. 18, 2014

(65) Prior Publication Data
US 2016/0175546 A1    Jun. 23, 2016

(51) Int. Cl.
| | | |
|---|---|---|
| *B05B 7/24* | (2006.01) | |
| *A61K 33/40* | (2006.01) | |
| *B65D 83/14* | (2006.01) | |
| *B65D 83/20* | (2006.01) | |
| *B65D 83/22* | (2006.01) | |
| *B05B 1/06* | (2006.01) | |
| *A61M 15/00* | (2006.01) | |

(52) U.S. Cl.
CPC .......... *A61K 33/40* (2013.01); *A61M 15/009* (2013.01); *B05B 1/06* (2013.01); *B05B 7/24* (2013.01); *B65D 83/206* (2013.01); *B65D 83/226* (2013.01); *B65D 83/75* (2013.01); *B65D 83/752* (2013.01)

(58) Field of Classification Search
CPC ......... B05B 7/24; B05B 7/241; B05B 7/2416; B65D 83/752; B65D 83/75
USPC ........................................................ 239/337
See application file for complete search history.

(56) References Cited

U.S. PATENT DOCUMENTS

| | | | | |
|---|---|---|---|---|
| 4,895,280 A * | 1/1990 | Tourigny | ............. | B65D 83/285 138/110 |
| 5,944,912 A * | 8/1999 | Jenkins | ................ | C11D 3/3947 134/40 |
| 2003/0205633 A1* | 11/2003 | Reizian | .................... | B44D 2/00 239/690 |
| 2008/0017671 A1* | 1/2008 | Shieh | ................... | B65D 83/752 222/394 |
| 2009/0277653 A1* | 11/2009 | Mori | ....................... | A62C 13/66 169/30 |
| 2011/0132936 A1* | 6/2011 | Weng | .................. | B65D 83/201 222/402.13 |
| 2011/0200683 A1* | 8/2011 | Piper | .................... | A61K 31/327 424/616 |

* cited by examiner

*Primary Examiner* — Arthur O Hall
*Assistant Examiner* — Tuongminh Pham (57) ABSTRACT

An aerosol hydrogen peroxide mixture agent with trigger sprayer that can be easily held in one hand. The hydrogen peroxide agent is in a bag inside a can and under pressure from air or nitrogen or mixture thereof, and can only be initially opened and released by pulling the tab of the trigger sprayer. The trigger assembly cannot be sprayed until the tab is pulled. The can is cylindrical canister housing and has a dip tube that goes to the bag of the can to the hydrogen peroxide mixture agent. There is propellant composed of air or nitrogen or mixture thereof in the can that pushes on the bag holding the hydrogen peroxide mixture agent up through the dip tube to the valve operative and then to the actuator stem up through the trigger sprayer.

16 Claims, 8 Drawing Sheets

AEROSOL HYDOGEN PEROXIDE MIXTURE WITH TRIGGER SPRAYER

CROSS-REFERENCE TO RELATED APPLICATIONS

None

FEDERALLY SPONSORED RESEARCH

None

SEQUENCE LISTING

None

BACKGROUND

Traditional way of treating cuts and bruises is the use of a large plastic bottle of Hydrogen Peroxide Mixture Agent pouring it on the wound that can be bulky and cumbersome to use. This invention addresses a new way treating wounds using an aerosol can and trigger sprayer that is both easy to use and fast. The Trigger Sprayer allows the user to be able to pull the tab with their index finger and spray a Hydrogen Peroxide Mixture Agent onto the wound to be treated. Initially when bought there is a tab that needs to be pulled so the Hydrogen Peroxide Mixture Agent is unused and not tampered with until ready to use. When the tab is not pulled the Hydrogen Peroxide Mixture Agent with Trigger sprayer cannot be sprayed. However when the tab is pulled it is opened and can be sprayed when needed. Additionally this invention can easily be held in one hand for ease of use and portability. Finally in emergency situations such as military combat and catastrophes treatment is needed on multiple people at a fast pace so having a trigger sprayer for delivering Hydrogen Peroxide Mixture Agent in a fast a rapid pace would be especially useful.

SUMMARY OF THE INVENTION

The invention is a Hydrogen Peroxide Mixture Agent with a trigger sprayer. In a preferred embodiment of the invention the trigger sprayer is fitted onto a mounting cup with a Valve Operative extending to a dip tube going to the bag inside the aerosol can holding the Hydrogen Peroxide Mixture Agent. The Direction Chamber allows the Hydrogen Peroxide Mixture Agent to flow through the trigger sprayer to the nozzle and out the Opening where it sprays out toward the area or wound to be treated. The Trigger pivots up and down that puts pressure on the Direction Chamber that puts pressure on the actuator stem that exerts pressure on the Valve Operative allowing the Hydrogen Peroxide Mixture Agent to flow up. The Opening on the trigger Assembly can is configured to allow the Hydrogen Peroxide Mixture Agent to flow out as a mist in a spray cone. There is a Propellant composed of nitrogen, air or mixture thereof inside the can that presses on the Bag that holds the Hydrogen Peroxide Mixture Agent. A Mounting Cup is placed in the Hole at the top of the Aerosol Can and holds the pressure of the Propellant and bag containing Hydrogen Peroxide Mixture Agent. The Mounting Cup of the aerosol can has a actuator stem that when it is depressed cause the Valve Operative to allow the Hydrogen Peroxide Mixture Agent pushed up and then to be sprayed out in a conical pattern. The propellant can be Nitrogen, Air or combination of each. The aerosol can is cylindrical. The Trigger sprayer of the aerosol Hydrogen Peroxide has a tab on top of it that can be easily be pulled off which allows the trigger to be depressed and ready to be used. When this tab is not pulled no Hydrogen Peroxide Mixture Agent can come out of the Aerosol Hydrogen Peroxide Mixture with trigger Sprayer for easy storage. The Tab has breakaway hinges and can be snapped off easily. The Trigger can be depressed by an index finger or other fingers to release the Hydrogen Peroxide Mixture Agent. The Trigger Sprayer has a nozzle wherein the Hydrogen Peroxide Mixture Agent can flow be sprayed out in a spray cone with a diameter of 5 and 7 inches at between 4 and 6 inches from the opening of the Nozzle of the Trigger Assembly. The Trigger Assembly having a Trigger for opening and closing the Valve Operative to selectively discharge the Hydrogen Peroxide Mixture Agent from the Opening on the Nozzle as a Mist Spray Cone; wherein the Trigger is operable by pulling the trigger towards the container using one's index finger for opening the Valve Operative and for closing the Valve Operative by releasing the trigger.

OPERATION OF THE INVENTION

When the Tab is not pulled the Trigger of the Aerosol Hydrogen Peroxide Mixture Agent is locked and cannot be sprayed. The operation of the Aerosol Hydrogen Peroxide Mixture Agent with trigger sprayer is when there is a medical emergency and it is needed for use, the user simply pulls the tab of the Aerosol Hydrogen Peroxide Mixture Agent Trigger Sprayer which is located on top and this enables the trigger assembly to be pushed down on the mounting cup that has a stem sticking up that when depressed allows the propellant in the can to exert pressure onto the bag inside the can containing the Hydrogen Peroxide Mixture Agent up through the stem through the Trigger Assembly through the Direction Chamber then up through to the Nozzle and through the opening toward the area to be medically treated. The Hydrogen Peroxide Mixture Agent comes out the opening with pressure in a mist and because the trigger has a nozzle the user can easily identify the direction to spray the Hydrogen Peroxide Mixture Agent.

DETAILED DESCRIPTION

Figure 1:
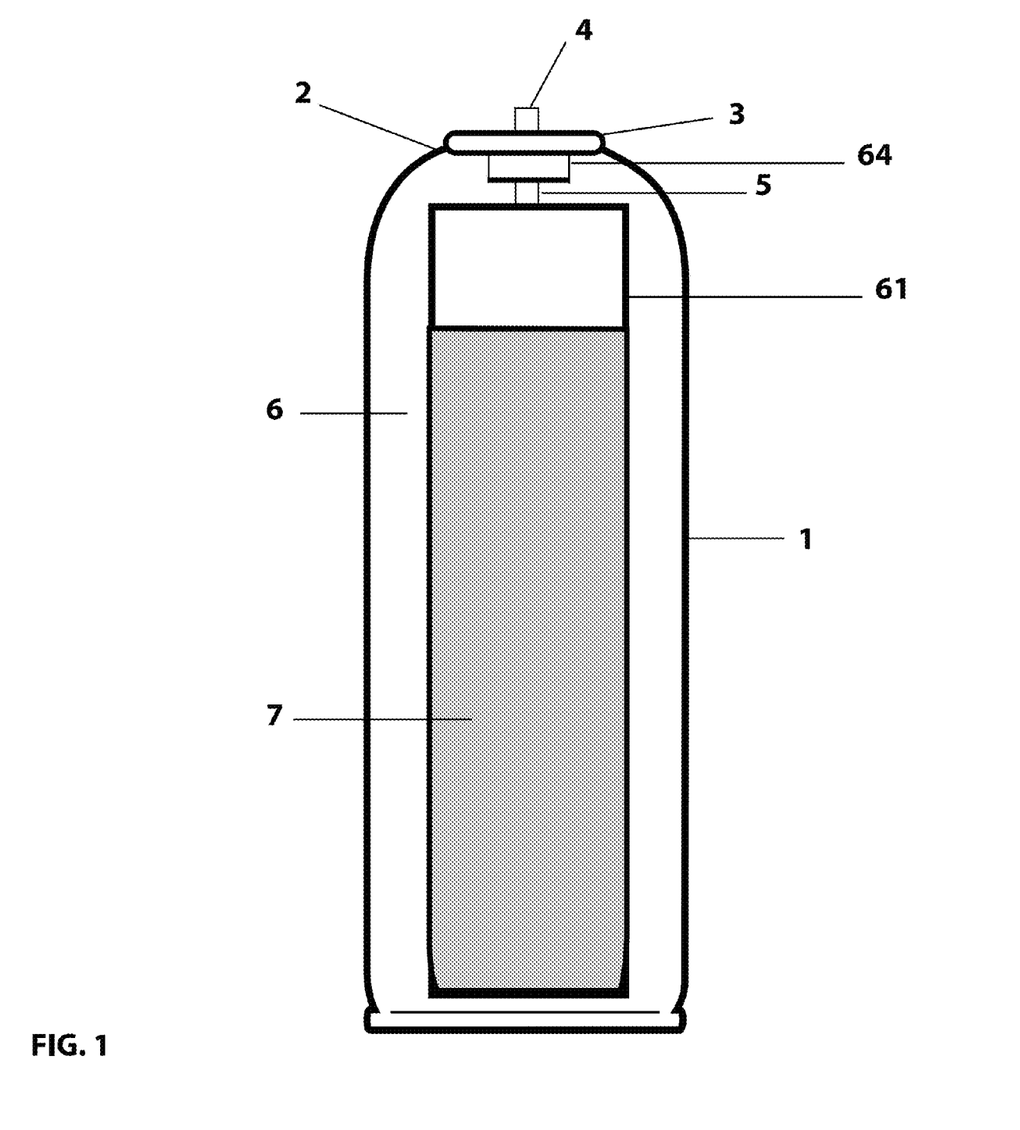
FIG. 1 shows a perspective view of only the Can with the Mounting Cup and Stem with the Bag holding the Hydrogen Peroxide Mixture Agent alone in a preferred embodiment of the invention.

Referring now to FIG. 1, a preferred embodiment of the invention is a Can 1 that is strong enough to withhold aerosol can pressure. The Can 1 has a Can Hole 2 at the top of the can. A Mounting Cup 3 at the top of the can is configured to fit on top of Can 1 into the Can Hole 2. The Mounting Cup 3 has a Actuator Stem 4 which is attached to it and a Valve Operative 64 that configured to attach to a Dip Tube 5 which extends to the Bag 61. The Bag 61 is filled partially with a Hydrogen Peroxide Mixture Agent 7 inside the Can 1. The Can 1 is also filled partially with a Propellant 6.

Figure 2:
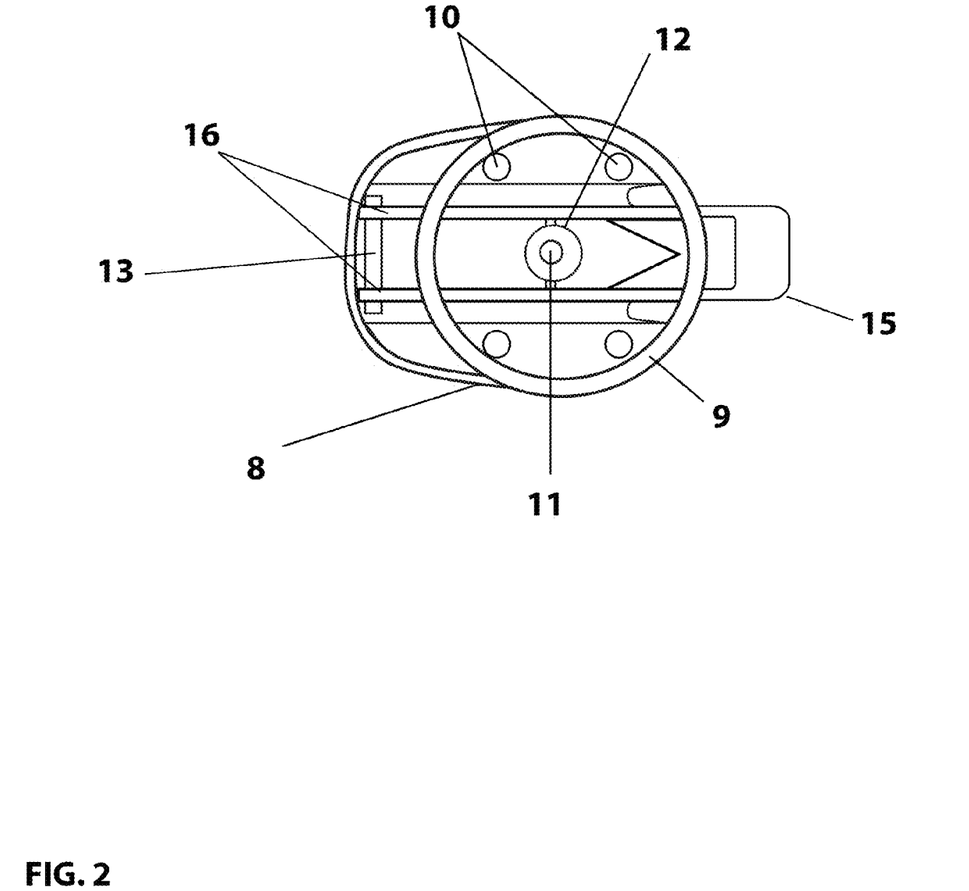
FIG. 2 shows a perspective view of the Trigger Assembly from the bottom of the Trigger Assembly in a preferred embodiment of the invention.

Referring now to FIG. 2 a preferred embodiment of the invention shows the bottom of a Trigger Assembly 8 in a preferred embodiment of the invention. The Trigger Assembly 8 has a Rim 9 configured to snap onto the Mounting Cup 3. The Trigger Assembly 8 also has one or more Fitting Units 10 that are configured to support and to grasp onto the Mounting Cup 3. The Trigger Assembly 8 has a Chamber Hole 11 which secures over the Actuator Stem 4. The Chamber Hole 11 leads into a Direction Chamber 12 and is attached to the back of the Trigger Assembly 8. A Trigger 15 is able to pivot up and down. The Trigger 15 uses a Trigger Pivoting Member 16 to pivot up and down and is held in place by a Trigger Pivoting Member Holder 13.

Figure 3:
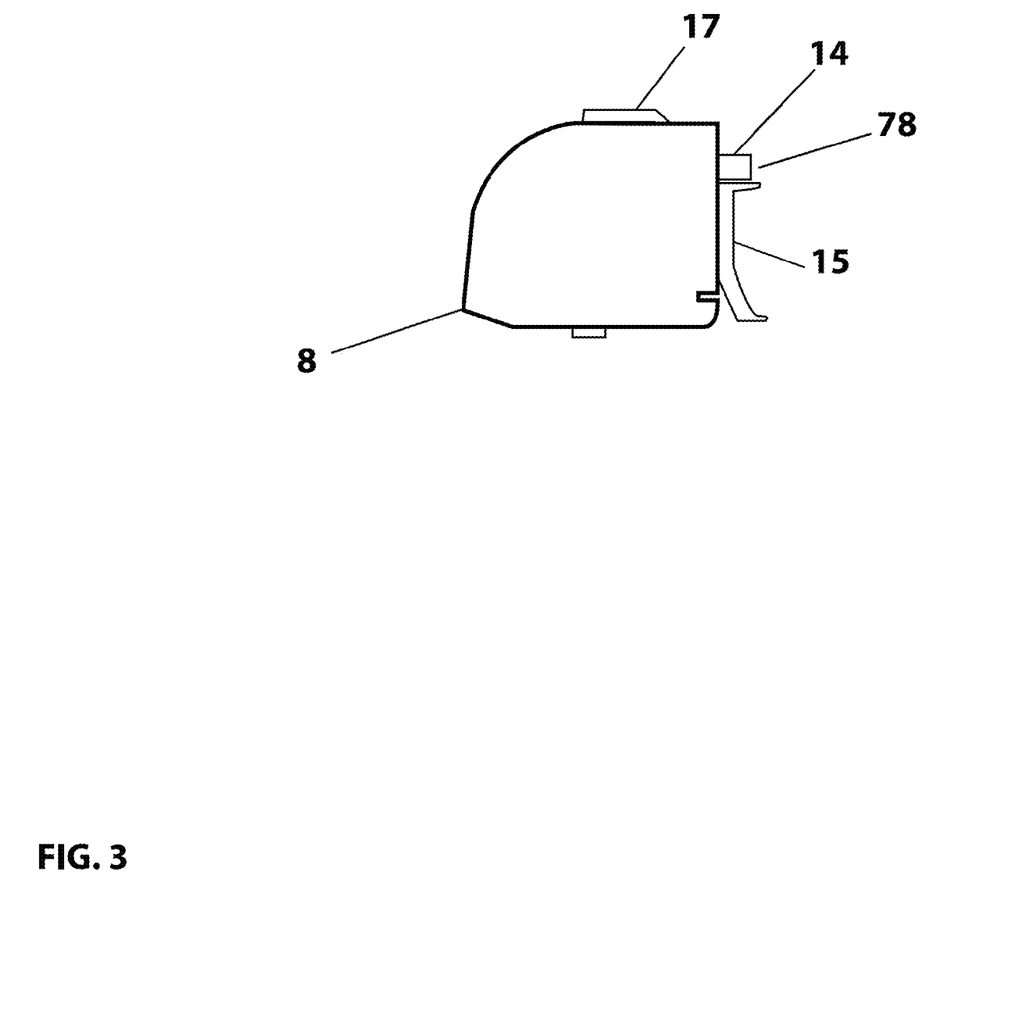
FIG. 3 shows a perspective side view of the Trigger Assembly with the tab intact, FIG. 4 Shows a cross sectional view of the Trigger Assembly with tab intact.

Referring now to FIG. 3 a preferred embodiment of the invention shows a perspective side view of the Trigger Assembly 8. A Tab 17 is fitted on top of the Trigger Assembly 8 which is attached to the Trigger 15 in a preferred embodiment of the invention. The Tab 17 must be removed for the Trigger 15 to move. A Nozzle 14 allows the user to point to where the spray will go. At the end of the Nozzle 14 there is a opening 78 which in the preferred embodiment of the invention has small holes to allow the Hydrogen Peroxide mixture Agent to come out in a mist.

Figure 4:
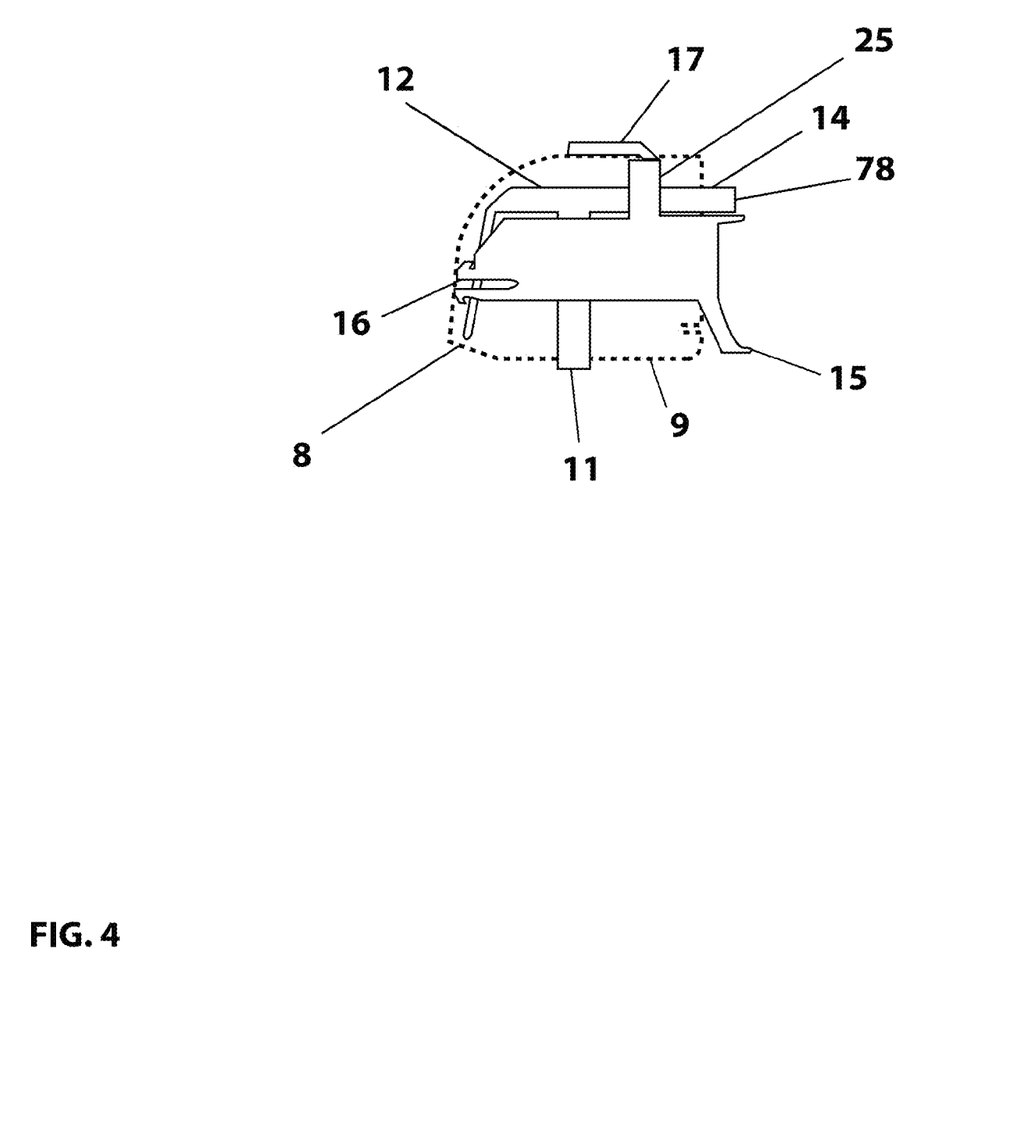

Referring now to FIG. 4 a cross sectional view of the Trigger Assembly 8. The Chamber Hole 11 is at the bottom and the Rim 9 can be seen that fits over the Mounting Cup 3. A Trigger 15 fits inside the Trigger Assembly 8. The Chamber Hole 11 goes into a Direction Chamber 12 which is hollow and allows the Hydrogen Peroxide Mixture Agent 7 to flow through Chamber Hole 11 into Direction Chamber 12 out a Nozzle 14 in a mist spray pattern. The Trigger 15 Pivots up and down by being pressed by an index finger and by way of its trigger Pivoting Member 16. The Trigger 15 has a Nozzle Holder 25 that holds onto the Nozzle 14. At the end of the nozzle is a Opening 78 with individual small holes to allow the Hydrogen Peroxide Mixture Agent to come out as a mist.

Figure 5:
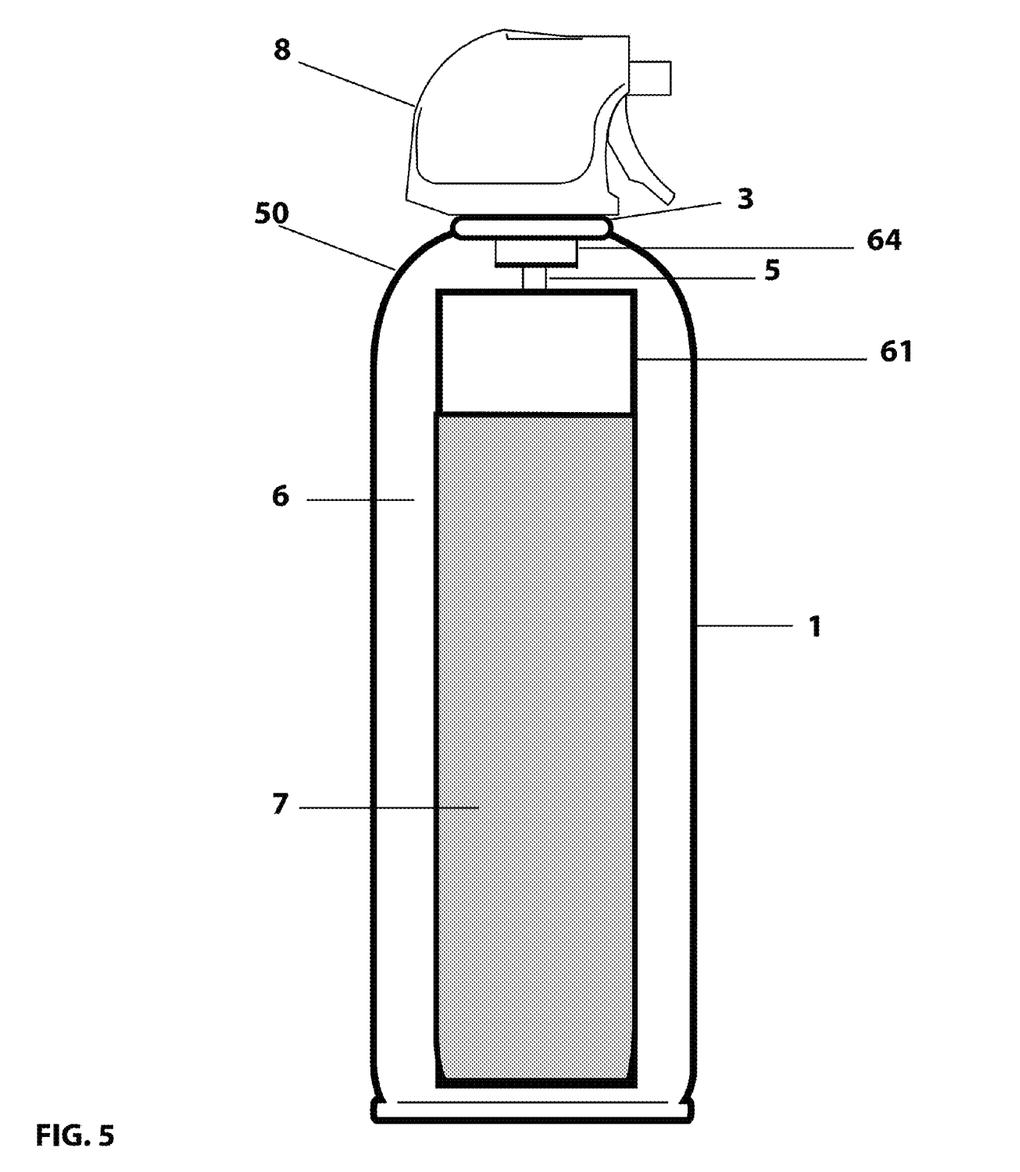
FIG. 5 shows Perspective Cross Sectional view of the Aerosol Hydrogen Peroxide Mixture Agent with a Trigger Assembly and tab intact in a preferred embodiment of the invention.

Referring now to FIG. 5 which shows a perspective side view of a Hydrogen Peroxide Mixture Agent with Trigger Sprayer. A Hydrogen Peroxide Mixture Agent with Trigger Sprayer Whole Unit 50 is shown as the whole invention. In this perspective view the Can 1 is shown filled with the Hydrogen Peroxide Mixture Agent. The Can 1 is filled with the Propellant 6 composed of nitrogen, air of mixture thereof and the Dip Tube 5 goes to the Bag 61 of the Hydrogen Peroxide Mixture Agent. The Dip Tube 5 then connects to the Valve Operative 64 which is configured to go through the Mounting Cup 3. A Mounting Cup 3 holds the pressure inside the Can 1. The Trigger Assembly 8 fits onto the Mounting Cup 3.

Figure 6:
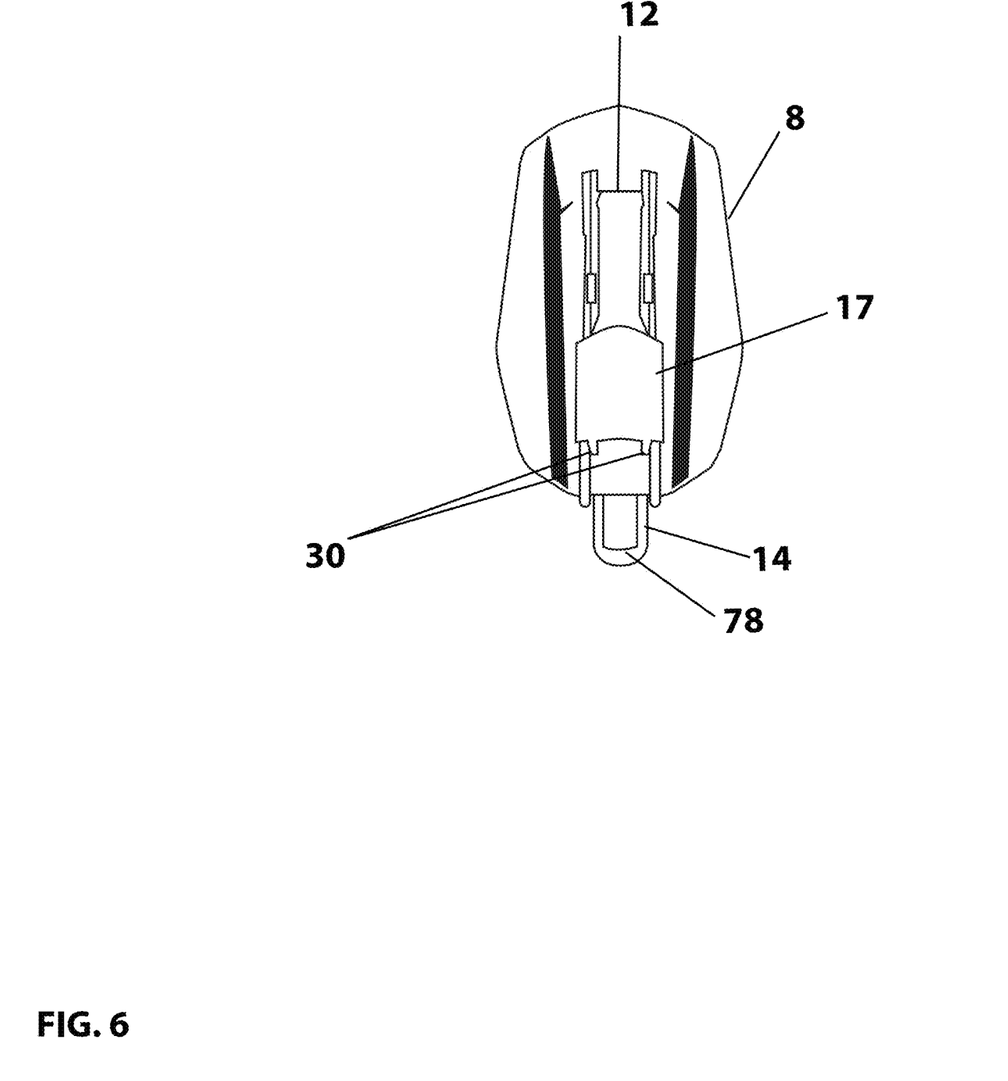
FIG. 6 shows a Perspective view of the Trigger Assembly looking from above.

Referring now to FIG. 6 shows a view of the Trigger Sprayer looking from above. The Tab 17 is shown as it sits on top of the Trigger Assembly 8. In this perspective view the tab has Breakaway Hinges 30 that allows the Tab 17 to be pulled off. When the Tab 17 is pulled off the Nozzle 14 and Direction Chamber 12 are free to move up and down as the Trigger 15 is pressed.

Figure 7:
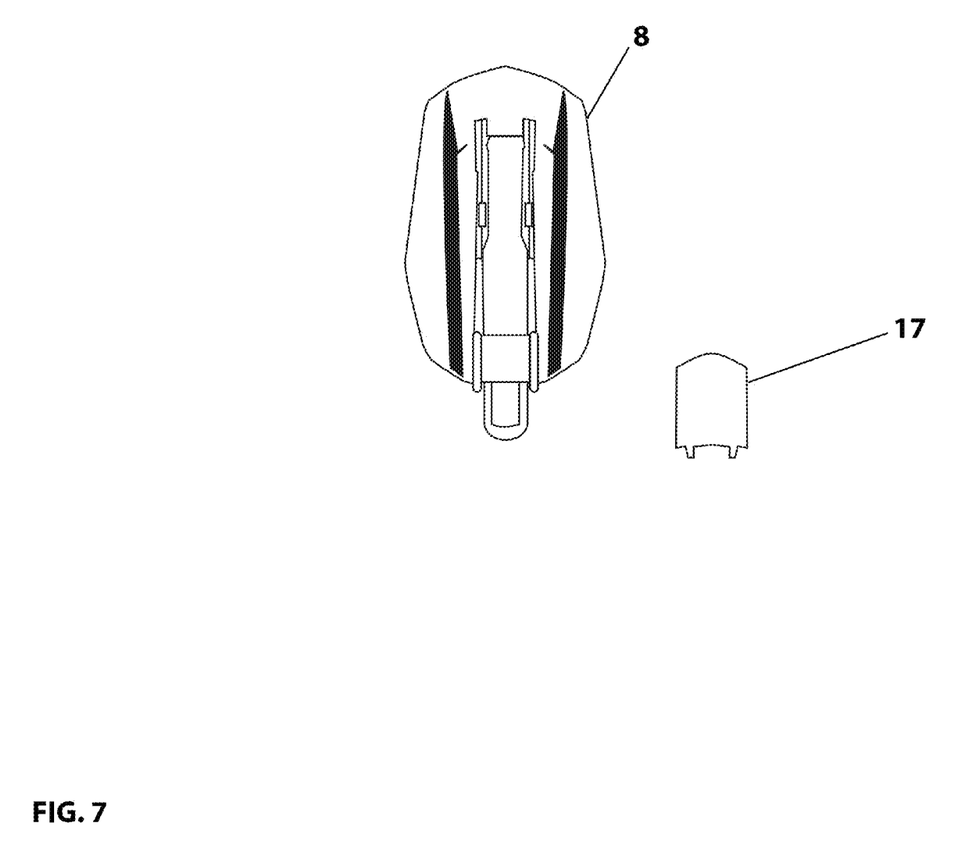
FIG. 7 shows a Perspective view of the Trigger Assembly looking from above with the Tab removed in a preferred embodiment of the invention.

Referring now to FIG. 7 shows a view of the Trigger Sprayer looking from above. The Tab 17 has been pulled for use after initial opening and allowing the Trigger Assembly 8 to be sprayed.

Figure 8:
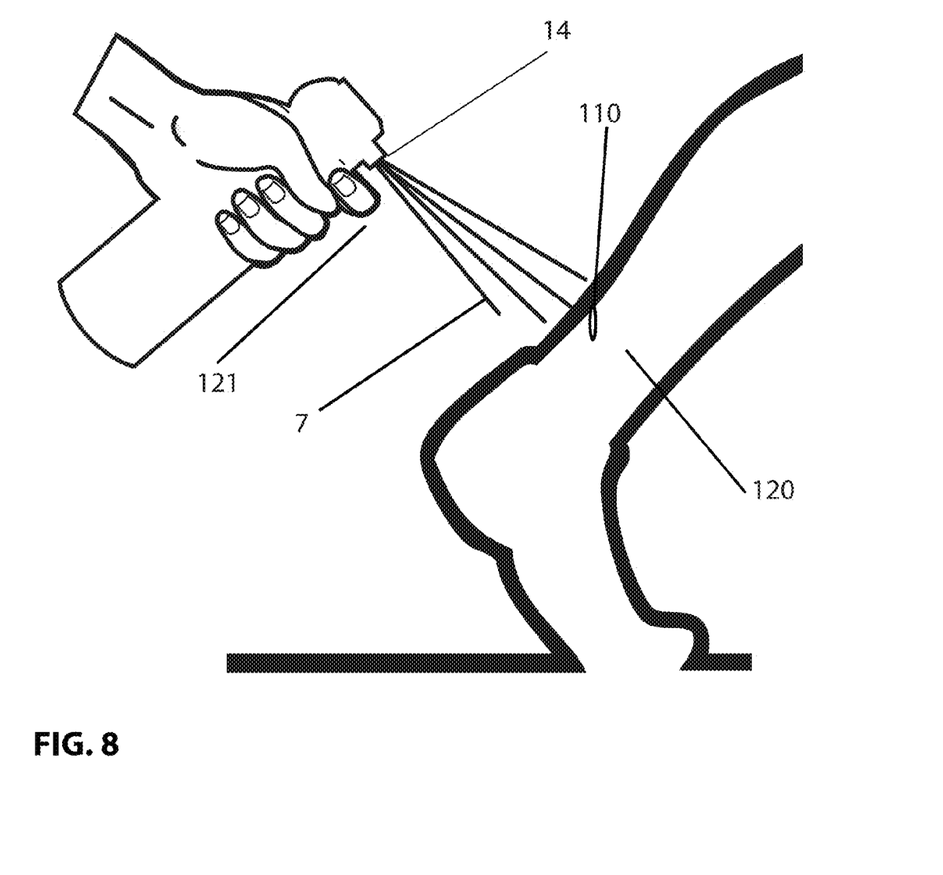
FIG. 8 shows the Perspective side view of the Aerosol Hydrogen Peroxide Mixture Agent with Trigger Assembly being held and used with index finder spraying a conical spray onto the wound of a leg that is being treated.

Referring to FIG. 8 shows a perspective view of a Index Finger 121 squeezing the trigger releasing the Hydrogen Peroxide Mixture Agent 7 through the Nozzle 14 onto a Wound 110 on a Persons Leg 120.

The invention claimed is:

1. An aerosol hydrogen peroxide mixture agent with a trigger sprayer comprising:
   a can storing Hydrogen Peroxide Mixture Agent in a bag under pressure from a propellant having an opening for discharge for Hydrogen Peroxide Mixture Agent there through;
   a valve for receiving the Hydrogen Peroxide Mixture Agent from the opening;
   a trigger assembly having a nozzle for discharging the Hydrogen Peroxide Mixture Agent from the can through the valve, the trigger assembly having a trigger for opening and closing the valve to selectively discharge the Hydrogen Peroxide Mixture Agent from an opening of the nozzle as a mist in a spray cone, wherein the spray cone has a diameter between 5 and 7 inches at between 4 and 6 inches from the opening of the nozzle of the trigger assembly wherein the trigger is configured to be pulled toward the can using one's index finger for opening the valve and the trigger is configured to be released for closing the valve;
   wherein the trigger is provided below the nozzle, and further comprises a nozzle holder portion extending vertically upward from below the nozzle to a portion above the nozzle, terminating at a position below a breakaway locking tab;
   the trigger pivots the nozzle about a hinge causing an actuator stem to release pressure causing the hydrogen peroxide mixture agent to flow up into a direction chamber and out the nozzle; and wherein
   wherein the hydrogen peroxide Mixture Agent comprises 2-5% hydrogen peroxide and 95%-98% percentage purified water or distilled water.

2. An aerosol hydrogen peroxide mixture agent with a trigger sprayer comprising:
   a can storing Hydrogen Peroxide Mixture Agent in a bag under pressure from a propellant having an opening for discharge for Hydrogen Peroxide Mixture Agent there through;
   a valve for receiving the Hydrogen Peroxide Mixture Agent from the opening;
   a trigger assembly having a nozzle for discharging the Hydrogen Peroxide Mixture Agent from the can through the valve, the trigger assembly having a trigger for opening and closing the valve to selectively discharge the Hydrogen Peroxide Mixture Agent from an opening of the nozzle as a mist in a spray cone, wherein the spray cone has a diameter between 5 and 7 inches at between 4 and 6 inches from the opening of the nozzle of the trigger assembly wherein the trigger is configured to be pulled toward the can using one's index finger for opening the valve and the trigger is configured to be released for closing the valve;

wherein the trigger is provided below the nozzle, and further comprises a nozzle holder portion extending vertically upward from below the nozzle to a portion above the nozzle;

a locking tab coupled to the nozzle holder portion to lock the trigger in place until a first initial use, and configured to be pulled off to unlock the trigger;

the trigger pivots the nozzle about a hinge causing an actuator stem to release pressure causing the hydrogen peroxide mixture agent to flow up into a direction chamber and out the nozzle; and wherein the hydrogen peroxide Mixture Agent comprises 2-5% hydrogen peroxide and 95%-98% percentage purified water or distilled water.

3. The sprayer as recited in claim 1 wherein the propellant comprises Nitrogen.

4. The sprayer as recited in claim 1 wherein the propellant comprises Oxygen.

5. The sprayer as recited in claim 1 wherein the propellant comprises a mixture of Oxygen and Nitrogen.

6. The sprayer as recited in claim 1 wherein the can is configured to hold up to 24 ounces of the hydrogen peroxide mixture agent.

7. The sprayer as recited in claim 1 wherein the Hydrogen Peroxide Mixture Agent comprises 3 percent Hydrogen Peroxide and 97 percent Purified water.

8. The sprayer as recited in claim 1 wherein the Hydrogen Peroxide Mixture Agent comprises 3 percent Hydrogen Peroxide and water added is distilled, artesian, mineral, public water source, purified, sparkling or spring water.

9. The sprayer as recited in claim 1 wherein the Hydrogen Peroxide Mixture Agent comprises 3 percent Hydrogen Peroxide and other percentage is water.

10. The sprayer as recited in claim 2, wherein the locking tab, when not removed, locks the Aerosol Hydrogen Peroxide Mixture Agent inside the can and prevents the mixture agent from being dispensed.

11. The sprayer as recited in claim 1, wherein the can has a longitudinal axis and the trigger is movable in a direction perpendicular to the longitudinal axis.

12. The sprayer as recited in claim 1 wherein the can is made of metal or plastic or both.

13. The sprayer as recited in claim 1 wherein the trigger assembly is made of metal or plastic or a combination of both.

14. The sprayer as recited in claim 1 wherein the hydrogen peroxide mixture agent with the trigger sprayer is a system for healing wounds.

15. The sprayer as recited in claim 1 wherein the spray cone has a diameter of 6 inches at 5 inches from the opening of the nozzle of the trigger assembly.

16. The sprayer as recited in claim 1 wherein the propellant is composed of 1,1,1,2-Tetrafluoroethane, Difluoroethane, Petroleum Hydrocarbon, C02, HFC1234ze, individually or mixture thereof.

* * * * *